United States Patent
Amari et al.

(10) Patent No.: US 7,838,534 B2
(45) Date of Patent: Nov. 23, 2010

(54) QUINUCLIDINE DERIVATIVES AS M3 ANTAGONISTS

(75) Inventors: Gabriele Amari, Parma (IT); Andrea Rizzi, Parma (IT); Riccardo Patacchini, Parma (IT); Valentina Cenacchi, Parma (IT); Gino Villetti, Parma (IT); Juan Lorenzo Catena Ruiz, Parma (IT); Isabel Masip Masip, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 144 days.

(21) Appl. No.: 11/881,146

(22) Filed: Jul. 25, 2007

(65) Prior Publication Data

US 2008/0039493 A1 Feb. 14, 2008

(30) Foreign Application Priority Data

Jul. 26, 2006 (EP) ................... 06117883

(51) Int. Cl.
 *A61P 11/00* (2006.01)
 *A61K 31/439* (2006.01)
(52) U.S. Cl. ...................... 514/305; 546/137
(58) Field of Classification Search ................. 546/137; 514/305
 See application file for complete search history.

(56) References Cited

FOREIGN PATENT DOCUMENTS

| WO | 02/00652 | | 1/2002 |
|---|---|---|---|
| WO | 02/051841 | | 7/2002 |
| WO | 02051840 | * | 7/2002 |
| WO | 03/053966 | | 7/2003 |
| WO | 03053966 | * | 7/2003 |
| WO | 04/000840 | | 12/2003 |
| WO | 2004000840 | * | 12/2003 |

OTHER PUBLICATIONS

Donfack Joseph., The Journal of allergy and clinical immunology, (Mar. 2003), vol. 111, No. 3, pp. 527-532.*

* cited by examiner

*Primary Examiner*—D. Margaret Seaman
*Assistant Examiner*—Niloofar Rahmani
(74) *Attorney, Agent, or Firm*—Ladas & Parry LLP

(57) ABSTRACT

Quinuclidine derivative of the general formula (I) in the form of single enantiomers or mixtures thereof are useful in the manufacture of a medicament for the prevention and therapy of respiratory diseases such as asthma, chronic obstructive pulmonary disease (COPD), chronic bronchitis, cough and emphysema

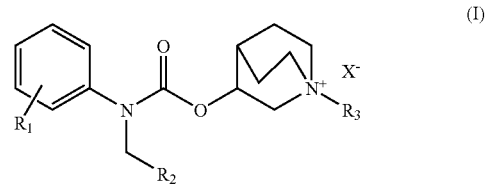

(I)

wherein:
$R_1$ is selected from H, F, Cl, Br, I and $(C_1$-$C_4)$-alkyl;
$R_2$ is optionally substituted 2- or 3-thienyl, or substituted phenyl;
$R_3$ is $(CH_2)_{1-4}$—$COR_4$ or $(CH_2)_{1-4}$—$S(O)_nR_4$, wherein $R_4$ is optionally substituted phenyl or optionally substituted 2- or 3-thienyl;
n is 0, 1 or 2;
$X^-$ is a pharmaceutically acceptable anion.

8 Claims, No Drawings

QUINUCLIDINE DERIVATIVES AS M3 ANTAGONISTS

FIELD OF THE INVENTION

The present invention relates to antimuscarinic agents, in particular to quinuclidine derivatives provided with adequate selectivity for the muscarinic M3-receptor and a long duration of action.

BACKGROUND OF THE INVENTION

Acetylcholine muscarinic receptors have been thoroughly studied for some time and it is now commonly acknowledged that the M3 receptor is responsible of the contractile effect of acetylcholine in the smooth muscle of intestinal tract, urinary bladder and bronchi. M3 antagonist are currently used in therapy to induce bronchodilation and inhibit gastrointestinal motility and urinary bladder contraction. However, in the above-mentioned tissues, M2 receptors are also present; since M2 receptors are a major population in the smooth cardiac muscle, in order to avoid side-effects on the cardiac muscle the research has focused on the finding of selective M3 antagonists.

Recently it has been reported that tiotropium, the first drug in a new generation of antimuscarinic drugs, possesses unique properties of "kinetic selectivity" with fast dissociation from M2 receptors and very slow dissociation from M1 and M3 receptors.

Therefore both good selectivity for, and slow dissociation from the M3 receptors are deemed important for new antimuscarinic drugs efficacious by inhalation in a once a day administration for the treatment of respiratory diseases and in particular inflammatory or obstructive airway diseases such as asthma and chronic obstructive pulmonary disease (COPD).

Selective M3 antagonists containing the quinuclidine nucleus are, for instance, disclosed in WO 02/00652, WO 02/051841, WO 03/053966 and WO 2004/000840.

In particular, WO 02/00652 and WO 03/053966 relate to quinuclidyl-carbamate derivatives provided with affinity for the human M3 receptor and selectivity for the M3 receptors over the M2 receptors.

WO 02/051841 and WO 2004/000840 disclose antimuscarinic quinuclidine derivatives showing high affinity and selectivity for the muscarinic M3 receptors over the M2 receptors, that, according to the inventors, also show bronchodilator activity in the test on bronchospasm in guinea pig, with high potency and a long duration of action, but no data are reported.

Therefore, the muscarinic antagonists of the prior art are mainly characterised by their selectivity for the M3 receptors over the M2 receptors and even though in WO 02/051841 and WO 2004/000840 it is also said in generic terms that the compounds are provided with a bronchodilator activity and a long duration of action, no demonstration is given.

SUMMARY OF THE INVENTION

The present invention relates to the use of an antimuscarinic agent, in particular to a quinuclidine derivative of the general formula (I) in the form of single enantiomers or mixtures thereof in the manufacture of a medicament for the prevention and therapy of respiratory diseases such as asthma, chronic obstructive pulmonary disease (COPD), chronic bronchitis, cough and emphysema

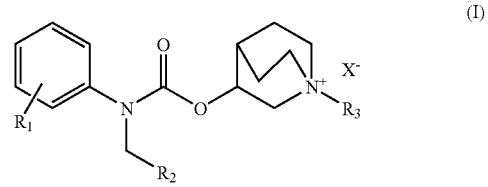

wherein:

$R_1$ is selected from H, F, Cl, Br, I and $(C_1\text{-}C_4)$-alkyl;

$R_2$ is 2- or 3-thienyl, optionally substituted with one or more substituents independently selected from F, Cl, Br, I and $(C_1\text{-}C_4)$-alkyl optionally substituted with one or more F or OH;

phenyl substituted with one or more substituents independently selected from F, Cl, Br, I, OH and $(C_1\text{-}C_4)$-alkyl optionally substituted with one or more F or OH;

$R_3$ is $(CH_2)_{1\text{-}4}\text{—}COR_4$ or $(CH_2)_{1\text{-}4}\text{—}S(O)R_4$, wherein $R_4$ is phenyl optionally substituted with one or more substituents independently selected from OH, $NO_2$, CN, F, Cl, Br, I, $NH_2$, $(C_1\text{-}C_5)$-alkanoylamino, $(C_1\text{-}C_4)$-alkyl, $(C_1\text{-}C_6)$-cycloakyl, $(C_1\text{-}C_4)$-alkoxyl, $(C_1\text{-}C_4)$-alkylthio, $(C_1\text{-}C_4)$-alkoxycarbonyl, optionally substituted phenyl or phenoxy;

2- or 3-thienyl, optionally substituted with one or more substituents independently selected from OH, $NO_2$, CN, F, Cl, Br, I, $NH_2$, $(C_1\text{-}C_5)$-alkanoylamino, $(C_1\text{-}C_4)$-alkyl, $(C_1\text{-}C_6)$-cycloakyl, $(C_1\text{-}C_4)$-alkoxyl, $(C_1\text{-}C_4)$-alkylthio, $(C_1\text{-}C_4)$-alkoxycarbonyl, optionally substituted phenyl or phenoxy;

n is 0, 1 or 2;

$X^-$ is a pharmaceutically acceptable anion.

The present invention relates also to particular quinuclidine derivatives in the form of single enantiomers or mixtures thereof belonging to formula (I) which are novel per se and are represented by: the formula (Ic)

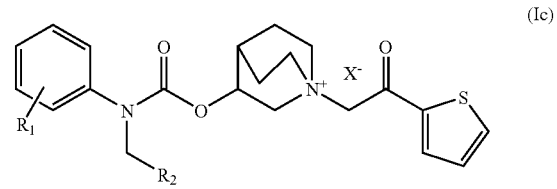

wherein $R_1$, in position 2 or 3, is selected from the group consisting of F, Cl, Br and I;

$R_2$ is 3,4,5-trifluorophenyl, 3,4-difluorophenyl, 2-hydroxyphenyl or 4-hydroxyphenyl;

$X^-$ is a pharmaceutically acceptable anion; the formula (Ib)

(Ib)

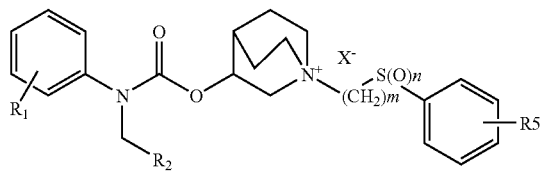

wherein
R$_1$, in position 2 or 3, is selected from the group consisting of F, Cl, Br and I;
R$_2$ is 3,4,5-trifluorophenyl or 4-fluorophenyl;
m is 1 or 2;
n is 0, 1 or 2;
R$_5$ is selected from the group consisting of H, CN, F, Cl, Br, I and (C$_1$-C$_4$)-alkoxyl;
X$^-$ is a pharmaceutically acceptable anion; and formula (Ia)

(Ia)

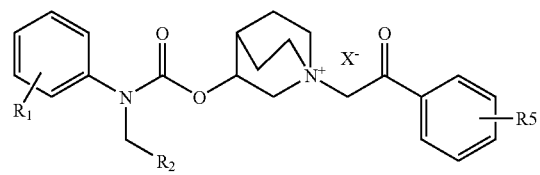

wherein
R$_1$, in position 2 or 3, is selected from the group consisting of F, Cl, Br, I and (C$_1$-C$_4$)-alkyl;
R$_2$ is selected from the group consisting of 2-hydroxyphenyl, 3-hydroxyphenyl, 4-hydroxyphenyl, 3,4,5-trifluorophenyl or 2,4,5-trifluorophenyl;
R$_5$ is selected from the group consisting of H, CN, F, Cl, Br, I and (C$_1$-C$_4$)-alkoxyl;
X$^-$ is a pharmaceutically acceptable anion.

Moreover the present invention relates to the use of a quinuclidine derivative of the general formula (Ia) and/or (Ib) and or (Ic) in the form of single enantiomers or mixtures thereof in the manufacture of a medicament for the prevention and therapy of respiratory diseases such as asthma, chronic obstructive pulmonary disease (COPD), chronic bronchitis, cough and emphysema.

In addition the present invention relates to a method for treating respiratory diseases such as asthma, chronic obstructive pulmonary disease (COPD), chronic bronchitis, cough and emphysema by administering a therapeutically effective amount of a compound of formula (I) and/or (Ia) and/or (Ib) and/or (Ic).

DESCRIPTION OF THE INVENTION

It has now been found that some particular quinuclidine derivatives, besides the affinity for the M3 muscarinic receptors, possess a long lasting bronchodilating activity due to their potent and prolonged interaction with the M3 muscarinic receptor and high lung retention.

Said quinuclidine derivatives are quinuclidine carbamate esters characterised by the fact that the nitrogen atom of the carbamate is substituted by an arylalkyl or heteroarylalkyl group selected from optionally substituted phenylmethyl, 2- or 3-thienylmethyl groups and the nitrogen atom of the quinuclidine ring is quaternarized with phenyl-carbonylalkyl, thienyl-carbonylalkyl or phenyl-thioalkyl groups.

Accordingly, the present invention relates, in a first embodiment, to the use of quinuclidine derivatives of the general formula (I) in the manufacture of a medicament for the prevention and therapy of respiratory diseases such as asthma, chronic obstructive pulmonary disease (COPD), chronic bronchitis, cough and emphysema.

(I)

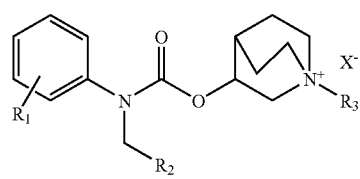

wherein:
R$_1$ is selected from H, F, Cl, Br, I and (C$_1$-C$_4$)-alkyl;
R$_2$ is
2- or 3-thienyl, optionally substituted with one or more substituents independently selected from F, Cl, Br, I and (C$_1$-C$_4$)-alkyl optionally substituted with one or more F or OH;
phenyl substituted with one or more substituents independently selected from F, Cl, Br, I, OH and (C$_1$-C$_4$)-alkyl optionally substituted with one or more F or OH;
R$_3$ is (CH$_2$)$_{1-4}$—COR$_4$ or (CH$_2$)$_{1-4}$—S(O)$_n$R$_4$, wherein R$_4$ is
phenyl optionally substituted with one or more substituents independently selected from OH, NO$_2$, CN, F, Cl, Br, I, NH$_2$, (C$_1$-C$_5$)-alkanoylamino, (C$_1$-C$_4$)-alkyl, (C$_1$-C$_6$)-cycloakyl, (C$_1$-C$_4$)—alkoxyl, (C$_1$-C$_4$)-alkylthio, (C$_1$-C$_4$)-alkoxycarbonyl, optionally substituted phenyl or phenoxy;
2- or 3-thienyl, optionally substituted with one or more substituents independently selected from OH, NO$_2$, CN, F, Cl, Br, I, NH$_2$, (C$_1$-C$_5$)-alkanoylamino, (C$_1$-C$_4$)-alkyl, (C$_1$-C$_6$)-cycloakyl, (C$_1$-C$_4$)-alkoxyl, (C$_1$-C$_4$)-alkylthio, (C$_1$-C$_4$)-alkoxycarbonyl, optionally substituted phenyl or phenoxy;
n is 0, 1 or 2.
X$^-$ is a pharmaceutically acceptable anion, preferably selected from chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate, and more preferably selected from chloride, bromide, formate, trifluoroacetate or methanesulfonate.

As the compounds of the invention have an asymmetric carbon on the quinuclidine carbon bound to the carbamic oxygen, they may be in the form of single enantiomers or mixtures thereof. The preferred compounds of the invention are optically active and are in the (R) configuration.

A first preferred embodiment of the invention comprises compounds of formula (Ia)

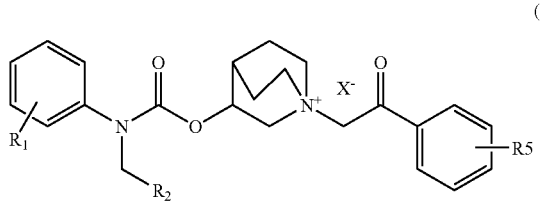

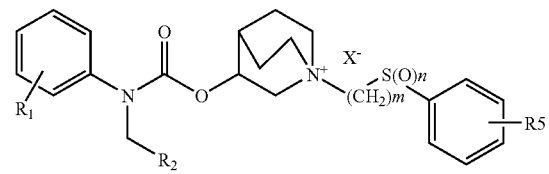

wherein
$R_1$, in position 2, 3 or 4, is selected from the group consisting of F, Cl, Br, I and $(C_1-C_4)$-alkyl;

$R_2$ is:
- 2-thienyl, optionally substituted with one or more substituents independently selected from the group consisting of F, Cl, Br, I, $(C_1-C_4)$-alkyl;
- phenyl, substituted with one or more substituents independently selected from the group consisting of F, Cl, Br, I and OH;

$R_5$ is selected from the group consisting of H, OH, $NO_2$, CN, F, Cl, Br, I, $(C_1-C_4)$-alkyl and $(C_1-C_4)$-alkoxyl.

Preferred compounds of formula (Ia) are those wherein:
$R_1$, in position 2 or 3, is selected from the group consisting of F, Cl, Br, I and $(C_1-C_4)$-alkyl;
$R_2$ is phenyl, substituted with one or more substituents independently selected from the group consisting of F, Cl, Br, I and OH;
$R_5$ is selected from the group consisting of H, OH, $NO_2$, CN, F, Cl, Br, I, $(C_1-C_4)$-alkyl and $(C_1-C_4)$-alkoxyl.

More preferred compounds of formula (Ia) are those wherein:
$R_1$, in position 2 or 3, is selected from the group consisting of F, Cl, Br, I and $(C_1-C_4)$-alkyl;
$R_2$ is selected from the group consisting of 2-hydroxyphenyl, 3-hydroxyphenyl, 4-hydroxyphenyl, 3,4,5-trifluorophenyl or 2,4,5-trifluorophenyl;
$R_5$ is selected from the group consisting of H, CN, F, Cl, Br, I and $(C_1-C_4)$-alkoxyl.

These compounds are also novel per se.

Representative compounds of the first preferred embodiment of the invention are:
(3R)-3-[(3-fluorophenyl)-(3,4,5-trifluorobenzyl)-carbamoyloxy]-1-(2-oxo-2-phenylethyl)-1-azoniabicyclo[2.2.2]octane, bromide [Compound 1]
(3R)-3-[2-fluorophenyl)-(3,4,5-trifluorobenzyl)-carbamoyloxy]-1-(2-oxo-2-phenylethyl)-1-azoniabicyclo[2.2.2]octane, bromide [Compound 2]
(3R)-3-[(3-fluorophenyl)-(3,4,5-trifluorobenzyl)-carbamoyloxy]-1-(2-oxo-2-(4-fluorophenyl)ethyl)-1-azoniabicyclo[2.2.2]octane, bromide [Compound 3].

A second preferred embodiment of the invention comprises compounds of formula (Ib)

wherein
$R_1$, in position 2 or 3, is selected from the group consisting of F, Cl, Br, I and $(C_1-C_4)$-alkyl;
$R_2$ is phenyl substituted with one or more substituents independently selected from the group consisting of F, Cl, Br and I;
m is 1 or 2;
n is 0, 1 or 2;
$R_5$ is selected from the group consisting of H, OH, $NO_2$, CN, F, Cl, Br, I, $(C_1-C_4)$-alkyl and $(C_1-C_4)$-alkoxyl.

Preferred compounds of formula (Ib) are those wherein
$R_1$, in position 2 or 3, is selected from the group consisting of F, Cl, Br and I;
$R_2$ is 3,4,5-trifluorophenyl or 4-fluorophenyl;
m is 1 or 2;
n is 0, 1 or 2
$R_5$ is selected from the group consisting of H, CN, F, Cl, Br, I and $(C_1-C_4)$-alkoxyl.

These compounds are also novel per se.

Representative compounds of the second preferred embodiment of the invention are:
(3R)-3-[(3-fluorophenyl)-(3,4,5-trifluorobenzyl)-carbamoyloxy]-1-(2-(phenylsulfanyl)ethyl)-1-azonia-bicyclo[2.2.2]octane, bromide [Compound 4]
(3R)-3-[(2-fluorophenyl)-(4-fluorobenzyl)-carbamoyloxy]-1-(phenylsulfanyl-methyl)-1-azonia-bicyclo[2.2.2]octane, bromide [Compound 5]

A third preferred embodiment of the invention comprises compounds of formula (Ic)

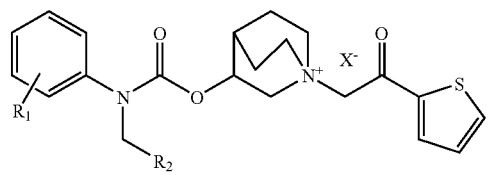

wherein
$R_1$, in position 2, 3 or 4, is selected from the group consisting of F, Cl, Br, I and $(C_1-C_4)$-alkyl;
$R_2$ is phenyl substituted with one or more substituents independently selected from the group consisting of F, Cl, Br, I and OH;

Preferred compounds of formula (Ic) are those wherein
$R_1$, in position 2 or 3, is selected from the group consisting of F, Cl, Br and I;
$R_2$ is 3,4,5-trifluorophenyl, 3,4-difluorophenyl, 2-hydroxyphenyl or 4-hydroxyphenyl.

These compounds are also novel per se.

Representative compounds of the third preferred embodiment of the invention are: (3R)-3-[(3-fluorophenyl)-(3, 4,5-trifluorobenzyl) carbamoyloxy]-1-(2-oxo-2- thiophen-2-ylethyl)-1-azoniabicyclo[2.2.2]octane bromide [Compound 6] and (3R)-3-[(3-fluorophenyl)-(3,4,5-trifluorobenzyl)carbamoyloxy]-1-(2-oxo-2-thiophen-2-ylethyl)-1-azoniabicyclo[2.2.2]octane chloride [Compound 7].

The compounds of the invention can be prepared according to the methods disclosed, for instance, in WO 03/053966.

In view of their potent and prolonged interaction with the M3 muscarinic receptor and of their long retention time in the lungs, the compounds of the invention can be used for the preparation of inhalation compositions for the prevention and therapy of respiratory diseases such as asthma, chronic obstructive pulmonary disease (COPD), chronic bronchitis, cough and emphysema.

Therefore, the present invention further relates to the use of the compounds of formula (I) for the preparation of pharmaceutical compositions for pulmonary administration comprising one or more pharmaceutically acceptable excipient or carrier.

Preferably the compounds of the invention, optionally in combination with one or more suitable carrier, vehicle or excipient, may be used for the preparation of inhalation compositions in the form of aqueous solutions or suspensions, pressurised hydrofluoroalkane solutions or suspensions, or of dry powder formulations.

As said before, the compounds are characterised by an adequate selectivity for the muscarinic M3 receptor and a long duration of action. For the purposes of the invention compounds with adequate selectivity for the muscarinic M3 receptor are those showing, in a binding test to human M2 and M3 muscarinic receptors, a M2/M3 receptor inhibition constants (Ki) ratio greater than 1.

Compounds endowed with a suitable duration of action are those for which, in the in vitro model of isolated guinea pig trachea, at a concentration of 10 nM, a percentage of the recovery of the contracting response to carbachol lower than 50%, four hours after the washout, has been detected, and whose bronchodilator activity in a guinea pig model of bronchospasm persisted unchanged up to 24 hours after the administration with percentages of inhibition higher than 50%. Moreover, as far as the evaluation of the duration of action is concerned, other important parameters were the lung retention, measuring the $MRT_L$ (Mean Residence Time in the Lung), i.e. the residence of the compound in the guinea pig lung after intratracheal administration of 10 nmol/kg, and the $C_{48}L/C_{0.5}L$ (%), i.e. the percentage of the amount of the compound in the lung 48 hours after intratracheal administration vs the amount the same compound in the lung 0.5 hours after administration. The compounds of the invention showed very slow lung elimination with $MRT_L$ higher than 10 hours and $C_{48}L/C_{0.5}L$ higher than 6%

The invention will be illustrated in greater detail in the following experimental section.

EXPERIMENTAL SECTION

Preparation Example (3R)-3-[(3-Fluorophenyl)-(3,4,5-trifluorobenzyl) carbamoyloxy]-1-(2-oxo-2-thiophen-2-yl-ethyl)-1-azoniabicyclo[2.2.2]octane bromide [Compound 6]

A solution of (3R)-(3-fluorophenyl)-(3,4,5-trifluorobenzyl)carbamic acid 1-aza-bicyclo[2.2.2]oct-3-yl ester hydrochloride (prepared as described in WO03/053966 as Intermediate 15) (1 g, 2.248 mmol) in water (5 ml) was added with an excess of sodium carbonate (1 g) in water (4 ml) and extracted with ethyl acetate (2×10 ml). The organic layer was dried over anhydrous sodium sulfate and evaporated under vacuum.

The resulting free base (750 mg, 1.836 mmol) was dissolved in acetonitrile (4 ml) and added dropwise with a solution of 2-bromo-1-thiophen-2-yl-ethanone (750 mg, 3.657 mmol) in chloroform (6 ml). The resulting solution was refluxed for 12 hours. The solvent was evaporated and the residue dissolved in acetonitrile (7.5 ml). Crystallisation occurred after some minutes of stirring. The solid was filtered, washed with acetonitrile (1 ml) and dried under vacuum at 45° C. 760 mg of the title compound was obtained as white solid.

Mother liquors were evaporated to dryness and purified by column chromatography ($SiO_2$, eluent: dichloromethane/methanol=95/5 to 80/20) to give further 120 mg of the title compound.

Analogously (3R)-3-[(3-fluorophenyl)-(3,4,5-trifluorobenzyl)carbamoyloxy]-1-(2-oxo-2-thiophen-2-yl-ethyl)-1-azoniabicyclo[2.2.2]octane chloride [Compound 7] was prepared starting from the free base of (3R)-(3-fluorophenyl)-(3,4,5-trifluorobenzyl)carbamic acid 1-aza-bicyclo[2.2.2]oct-3-yl ester by reaction with 2-chloro-1-thiophen-2-yl-ethanone.

Other compounds of the invention can be prepared with analogous procedures as in the preparation example.

Biological Characterisation

The interaction with M3 muscarinic receptors can be estimated by the results of in vitro studies which evaluated the potency of the test compounds and the offset of the inhibitory activity produced after washout of the antagonists in isolated guinea pig trachea and by the in vivo duration of action against acetylcholine-induced bronchospasm in the guinea pig.

In Vitro Interaction with the M3 Receptors

The potency of the antagonist activity in isolated guinea pig trachea was investigated following a method previously described by Haddad E B et al. in Br J Pharmacol 127, 413-420, 1999, with few modifications.

A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction (IC50) was taken as a measure of its potency in this bioassay.

In the experiments aiming at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 µM) was administered again (at 30 min interval between washout and next administration) during the next 4 hours.

After the administration of carbachol, the inhibitory effects of the compounds of the invention, administered at a concentration of 10 nM, was expressed as percentage of the recovery of the contracting response to carbachol. The percentage of recovery four hours after the washout was lower than 50%.

In Vivo Studies

The in vivo tests on acetylcholine-induced bronchospasm in guinea pig were performed according to H. Konzett H and Rossler F Arch Exp Path Pharmacol 195, 71-74, 1940. Aqueous solutions of the test compounds were instilled intratracheally in anaesthetised mechanically ventilated guinea pigs.

Bronchial response to intravenous acetylcholine challenge was determined before and after drug administration and changes in pulmonary resistance at several time-points were expressed as percent of inhibition of bronchospasm.

The bronchodilator activity of the tested compounds persisted unchanged up to 24 hours after the administration.

Kinetic Characterisation: Lung Retention

Lung retention was measured by means of two parameters: the $MRT_L$ (Mean Residence Time in the Lung), i.e. the residence of the compound in the lung, which is the time of the last measurable concentration of the compound in the guinea pig lung after intratracheal administration of 10 nmol/kg, determined after lung homogenization, and the $C_{48}L/C_{0.5}L$ (%), i.e. the percentage of the amount of the compound in the lung 48 hours after intratracheal administration vs the amount the same compound in the lung 0.5 hours after administration.

$MRT_L$ and $C_{48}L/C_{0.5}L$ (%) are two meaningful and predictive parameters of the duration of a drug's effect after single dose pulmonary administration.

The compounds of the invention showed very slow lung elimination with $MRT_L$ higher than 10 hours and $C_{48}L/C_{0.5}L$ higher than 6%.

In the same tests tiotropium bromide, utilized as reference compound, showed a $MRT_L$ of 7.1 hours and a $C_{48}L/C_{0.5}L$ of 2.3%, whereas another known antimuscarinic, ipratropium bromide, showed a $MRT_L$ of 3.9 hours and a $C_{48}L/C_{0.5}L$ of 0.3%.

In addition to having high lung retention no plasma levels of the present compounds were detected. These results would suggest that the compounds of the invention are retained in the lung and do not reach the systemic circulation. Therefore, potential undesirable secondary effects in other tissues could be avoided.

The invention claimed is:

1. A quinuclidine derivative of formula (Ic) in the form of a single enantiomers or a mixture thereof

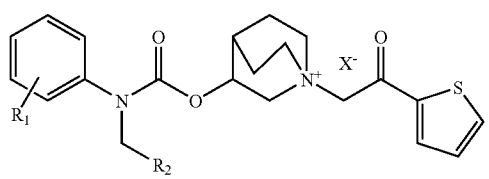

(Ic)

wherein
 $R_1$, in position 2 or 3, is selected from the group consisting of F, Cl, Br and I;
 $R_2$ is 3,4,5-trifluorophenyl, 3,4-difluorophenyl, 2-hydroxyphenyl or 4-hydroxyphenyl;
 $X^-$ is a pharmaceutically acceptable anion.

2. A quinuclidine derivative according to claim 1, wherein the quinuclidine carbon bound to the carbamic oxygen is optically active and is in the (R) configuration.

3. A quinuclidine derivative according to claim 1, wherein $X^-$ is an anion selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

4. A quinuclidine derivative selected from the group consisting of:
 (3R)-3-[(3-fluorophenyl)-(3,4,5-trifluorobenzyl)carbamoyloxy]-1-(2-oxo-2-thiophen-2-ylethyl)-1-azoniabicyclo[2.2.2]octane bromide; and
 (3R)-3-[(3-fluorophenyl)-(3,4,5-trifluorobenzyl)carbamoyloxy]-1-(2-oxo-2-thiophen-2-yl-ethyl)-1-azoniabicyclo[2.2.2]octane chloride.

5. A pharmaceutical composition for pulmonary administration comprising a therapeutically effective amount of a quinuclidine derivative according to claim 1 and one or more pharmaceutically acceptable excipient or carrier.

6. A method for treatment of a respiratory disease in a patient comprising (a) providing a quinuclidine derivative of the general formula (Ic) in the form of a single enantiomers or a mixture thereof

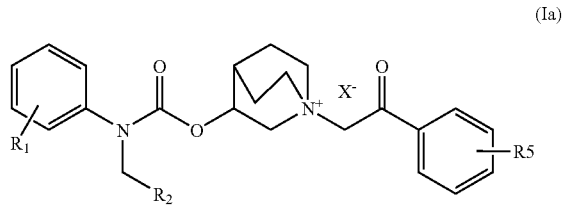

(Ia)

wherein:
 $R_1$ is in position 2 or 3 and is selected from H, F, Cl, Br, and I;
 $R_2$ is 3,4,5-trifluorophenyl, 3,4-difluorophenyl, 3-hydroxyphenyl or 4-hydroxyphenyl
 $X^-$ is a pharmaceutically acceptable anion; and (b) administering a therapeutically effective amount of the quinuclidine derivative to the patient
 wherein
 the respiratory disease is selected from the group consisting of asthma, chronic obstructive pulmonary disease and emphysema, and
 the quinuclidine derivative is provided to the patient through pulmonary administration by inhalation.

7. The method according to claim 6 wherein $X^-$ is an anion selected from chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

8. The method according to claim 6, wherein the quinuclidine carbon bound to the carbamic oxygen is optically active and is in the (R) configuration.

* * * * *

UNITED STATES PATENT AND TRADEMARK OFFICE
CERTIFICATE OF CORRECTION

PATENT NO.        : 7,838,534 B2
APPLICATION NO.   : 11/881146
DATED             : November 23, 2010
INVENTOR(S)       : Gabriele Amari et al.

It is certified that error appears in the above-identified patent and that said Letters Patent is hereby corrected as shown below:

In the Claims

Column 10, lines 25-33 (i.e. the chemical formula in claim 6) should read:

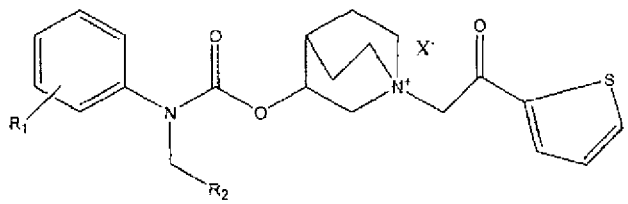

Signed and Sealed this
Fourth Day of March, 2014

Michelle K. Lee
*Deputy Director of the United States Patent and Trademark Office*